(12) United States Patent
Bagley et al.

(10) Patent No.: US 12,232,740 B2
(45) Date of Patent: Feb. 25, 2025

(54) TISSUE CLIP DEVICES, SYSTEMS, AND TRACTION METHODS

(71) Applicant: Boston Scientific Scimed, Inc., Maple Grove, MN (US)

(72) Inventors: Kevin L. Bagley, Natick, MA (US); Ramon Estevez, Lowell, MA (US); Nestor A. Ibanez, Brighton, MA (US); Danny S. Lee, Cambridge, MA (US); John Unger, Wrentham, MA (US); Ryan V. Wales, Northborough, MA (US); Talha Riaz, Framingham, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 164 days.

(21) Appl. No.: 17/475,852

(22) Filed: Sep. 15, 2021

(65) Prior Publication Data
US 2022/0000485 A1   Jan. 6, 2022

Related U.S. Application Data

(63) Continuation of application No. 15/930,604, filed on May 13, 2020, now Pat. No. 11,147,564.
(Continued)

(51) Int. Cl.
*A61B 17/122*   (2006.01)
*A61B 17/128*   (2006.01)

(52) U.S. Cl.
CPC ........ *A61B 17/1227* (2013.01); *A61B 17/128* (2013.01)

(58) Field of Classification Search
CPC ... A61B 17/1227; A61B 17/128; A61B 17/08; A61B 17/083; A61B 17/10; A61B 17/12;
(Continued)

(56) References Cited

U.S. PATENT DOCUMENTS 5,242,456 A * 9/1993 Nash ................. A61B 17/0218
606/151
5,569,274 A   10/1996 Rapacki et al.
(Continued)

FOREIGN PATENT DOCUMENTS

EP   3155955 A1   4/2017
WO   9309721 A1   5/1993
(Continued)

OTHER PUBLICATIONS

International Search Report and Written Opinion for the International Patent Application No. PCT/US2020/032575, dated Jun. 26, 2020, 13 pages.

*Primary Examiner* — Sarah A Long
*Assistant Examiner* — James R McGinnity
(74) *Attorney, Agent, or Firm* — Seager, Tufte & Wickhem, LLP

(57) ABSTRACT

The present disclosure pertains to medical devices. More particularly, the present disclosure pertains to tissue clip devices and related systems and methods. In an embodiment, a tissue clip may include a grasper including jaws at a first end, and a spring portion at a second end, and a longitudinal axis extending along a length of the grasper from the first end to the second end, wherein the spring portion is configured to bias the jaws toward each other. A wedge may be slidably disposed between the jaws such that an apex of the wedge is oriented toward the spring portion. A filament may be coupled to the wedge at a first end of the filament and may extend through a channel of the spring portion of the grasper to a second end of the filament.

18 Claims, 15 Drawing Sheets

Related U.S. Application Data

(60) Provisional application No. 62/847,599, filed on May 14, 2019.

(58) Field of Classification Search
CPC .............. A61B 17/122; A61B 17/1285; A61B 2017/081; A61B 2017/086; A61B 2017/088; A61F 6/20
See application file for complete search history.

(56) References Cited

U.S. PATENT DOCUMENTS

| | | |
|---|---|---|
| 8,172,859 B2 | 5/2012 | Matsuno et al. |
| 8,852,088 B2 | 6/2014 | Ransden et al. |
| 9,289,216 B2 | 3/2016 | Weisshaupt et al. |
| 9,974,532 B2 | 5/2018 | Baas et al. |
| 10,143,459 B2 | 12/2018 | Heftman |
| 10,524,786 B2 | 1/2020 | Khan |
| 2002/0177861 A1* | 11/2002 | Sugiyama ............ A61B 17/122 606/151 |
| 2012/0116419 A1 | 5/2012 | Sigmon |
| 2014/0023593 A1 | 1/2014 | Hadden |
| 2014/0243586 A1 | 8/2014 | Rohaninejad et al. |
| 2016/0354101 A1* | 12/2016 | Melsheimer ........... A61B 17/29 |
| 2017/0119234 A1* | 5/2017 | Petroskey .......... A61B 17/0218 |
| 2018/0035997 A1 | 2/2018 | Smith et al. |
| 2018/0263614 A1 | 9/2018 | Lee et al. |
| 2020/0129181 A1* | 4/2020 | Carrillo, Jr. ........ A61B 17/1227 |

FOREIGN PATENT DOCUMENTS

| | | | |
|---|---|---|---|
| WO | 9713466 A1 | 4/1997 |
| WO | 2010120812 A1 | 10/2010 |

\* cited by examiner

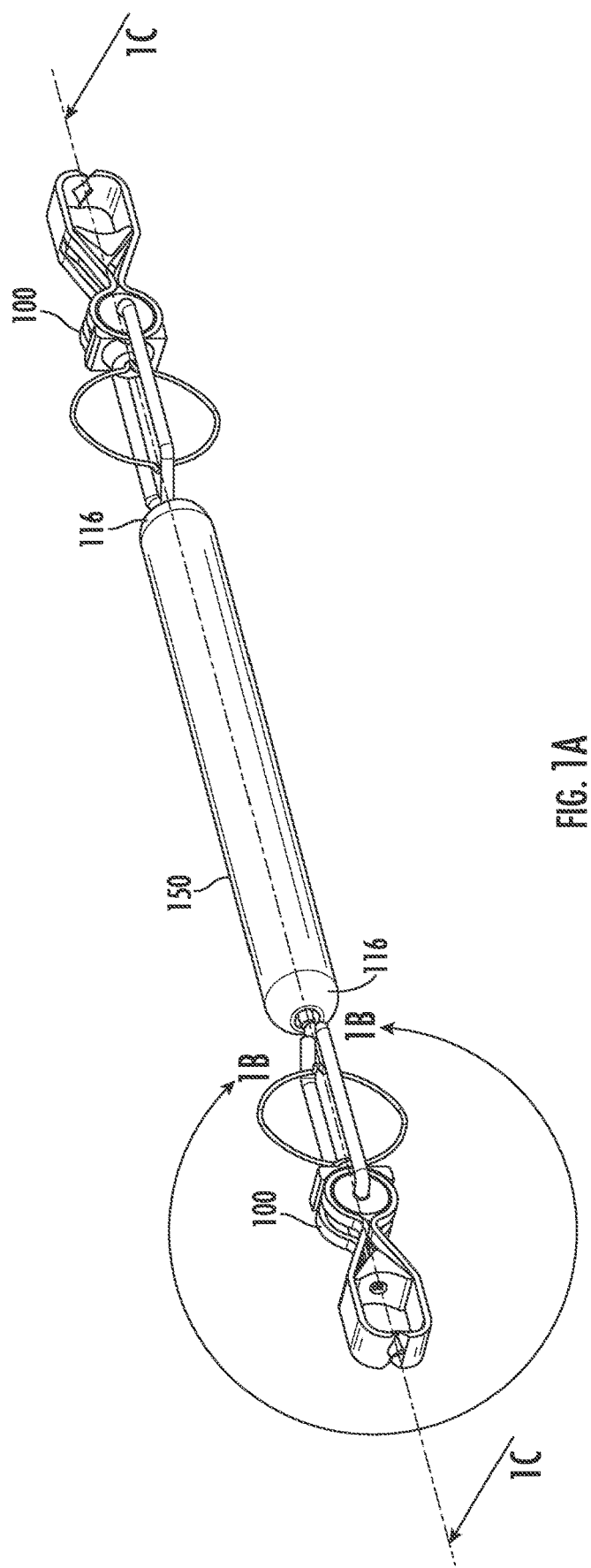

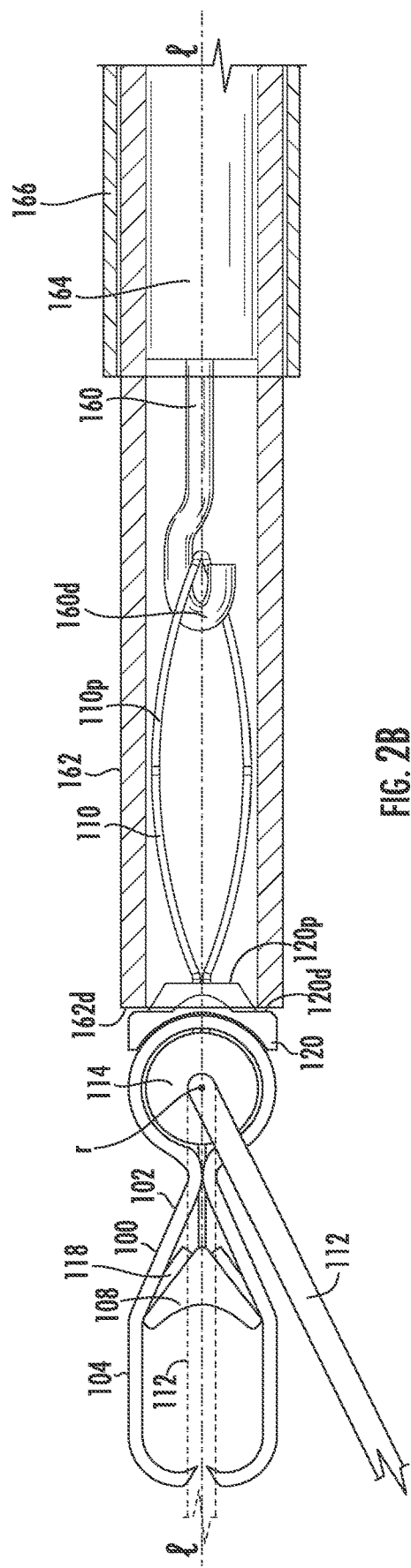

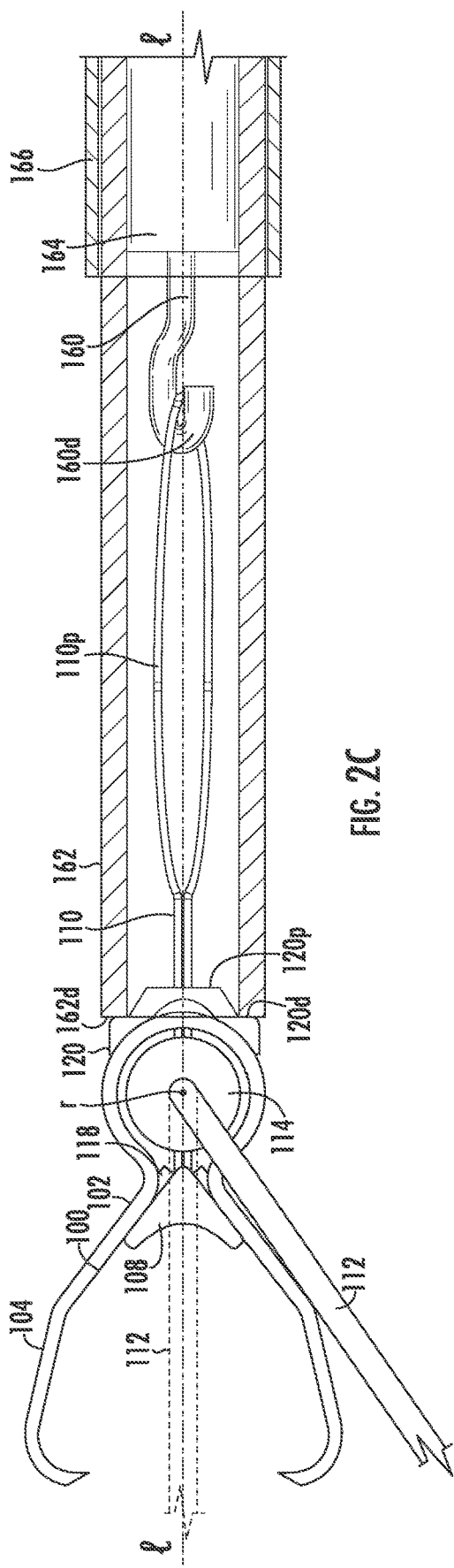
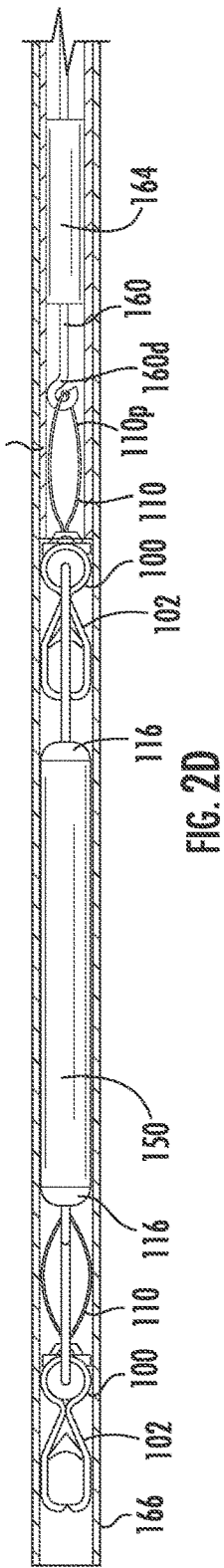
FIG. 2C
FIG. 2D

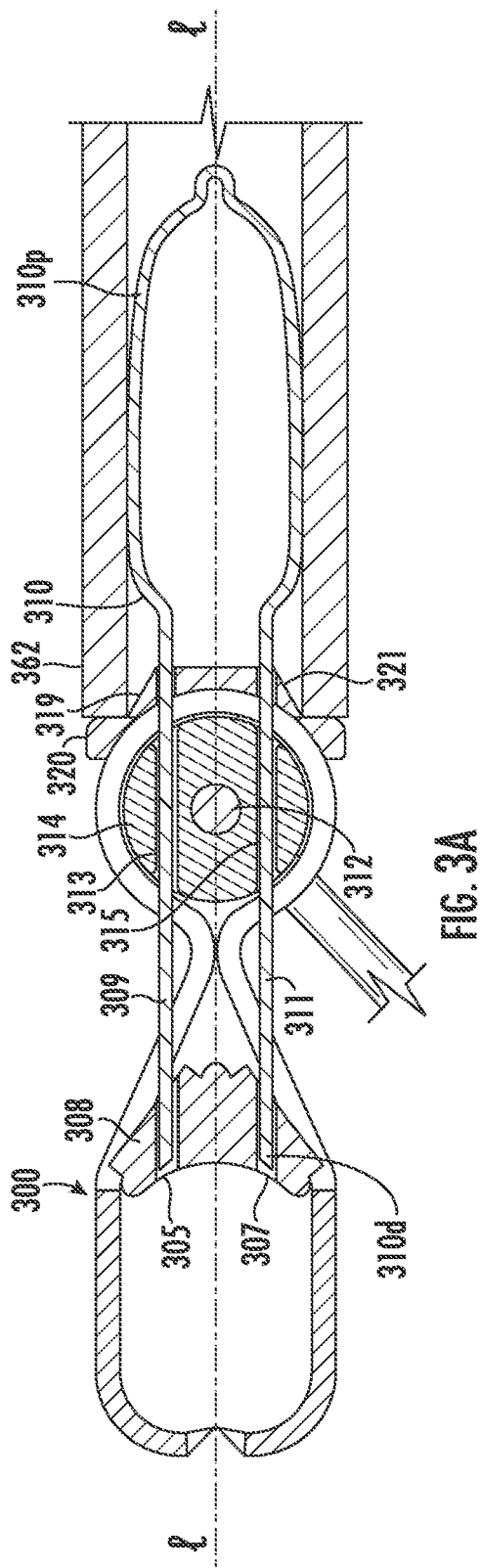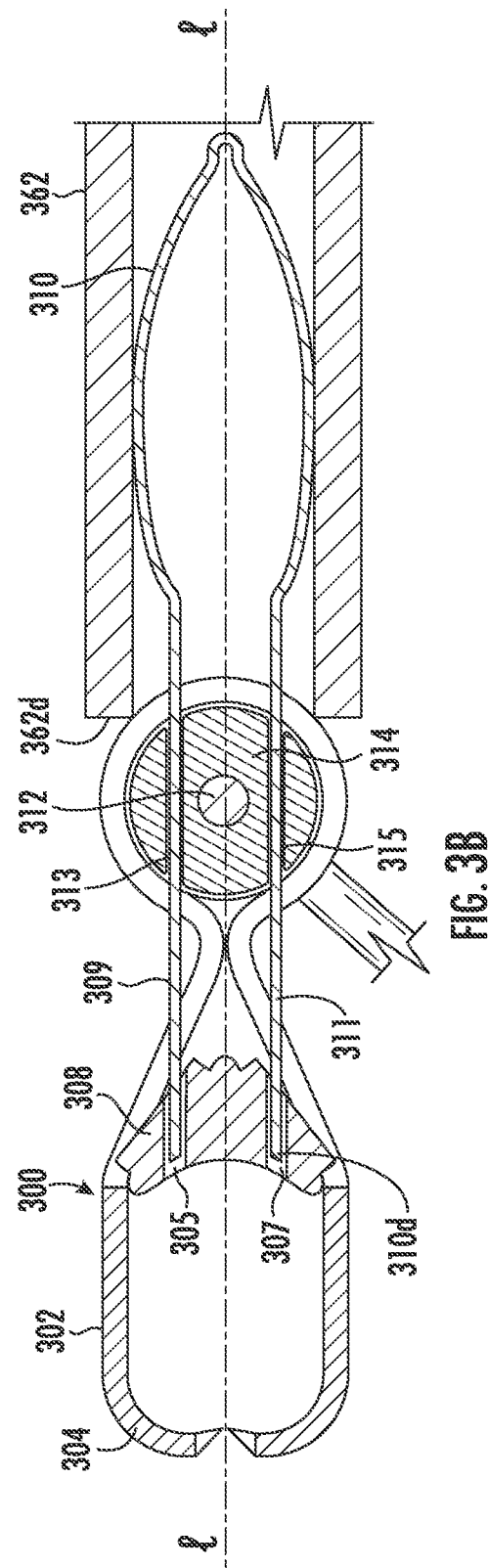

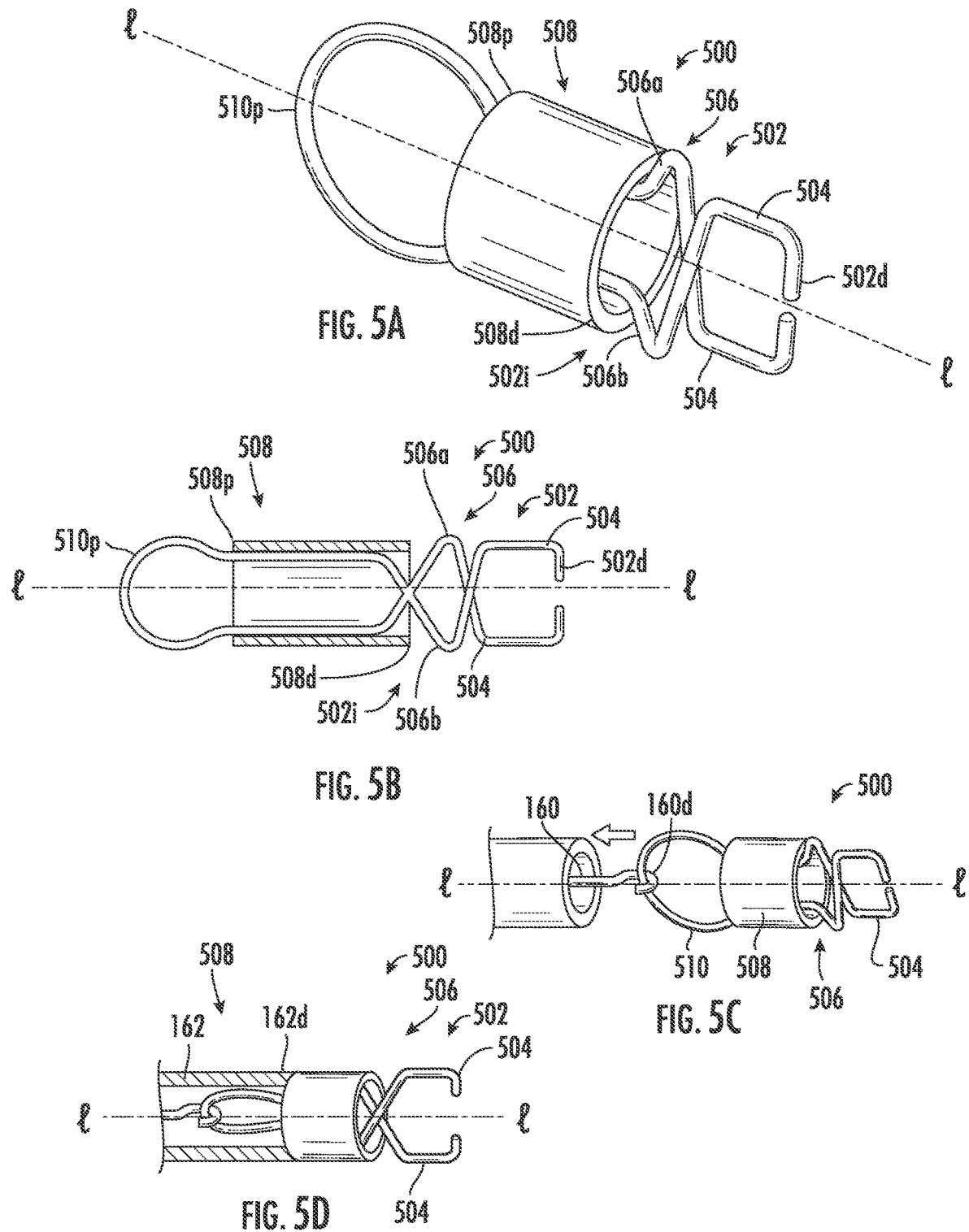

TISSUE CLIP DEVICES, SYSTEMS, AND TRACTION METHODS

CROSS-REFERENCE TO RELATED APPLICATIONS

This application is a continuation of Ser. No. 15/930,604, filed May 13, 2020, which claims the benefit of priority under 35 U.S.C. § 119 to U.S. Provisional Patent Application 62/847,599, filed May 14, 2019, which applications are incorporated herein by reference in their entireties for all purposes.

FIELD

The present disclosure pertains to medical devices. More particularly, the present disclosure pertains to tissue clip devices and related retraction/traction systems and methods.

BACKGROUND

Physicians are becoming more proficient at removing lesions from the gastrointestinal tract. However, with currently available technologies, conducting more complex procedures, such as endoscopic submucosal dissection (ESD), can be difficult and time consuming. Manipulating devices for clipping tissue may require procedurally complicated and/or time-intensive techniques for positioning and orienting the devices and associated medical instruments. For example, endoscopic submucosal dissection (ESD) is a procedure that enables tissue resection within the gastrointestinal tract. In addition, non-ideal visualization and lack of tissue tension also make the procedures difficult and time consuming. Having a means to create more significant traction force on the tissue would be desirable to improve the visualization of the cutting plane.

It is with the above considerations in mind that the improvements of the present disclosure may be useful.

SUMMARY

The present disclosure, in its various aspects, is directed generally to medical devices, and more specifically to tissue clip devices, retraction/traction methods, and related delivery systems. Embodiments according to the present disclosure, including as described herein, may decrease complications around tissue resection procedures, such as visualization, procedure time, and procedure complexity.

Various embodiments of a tissue clip are disclosed comprising a grasper including jaws at a first end. A spring portion may be at a second end. The grasper may extend a length from the first end to the second end along a longitudinal axis. The spring portion may be configured to bias the jaws toward each other. In some embodiments, a wedge may be slidably disposed between the jaws. An apex of the wedge may be oriented toward the spring portion. A filament may be coupled to the wedge at a first end of the filament. The filament may extend through a channel of the spring portion of the grasper to a second end of the filament. In alternate embodiments, a spring actuator and the spring portion are movable substantially axially relative to each other to cause the spring portion to move the jaws apart. The spring portion may have one or more ramps engaging the spring actuator to cause the jaws to move apart. The spring actuator may be a capsule or cylinder or collar.

In various embodiments a retainer may be disposed within the second end of the grasper. A hinge may be at least partially extending through the retainer. A retainer may be rotatable about the hinge. A first end of the hinge may be disposed within the retainer. A second end of the hinge may include an attachment member configured to attach to a tether. A plurality of channels may extend through the retainer parallel to the longitudinal axis. Portions of the filament may be extendable through the plurality of channels. A tab may be disposed on the wedge. The tab may be slidable within a slot that extends along at least a portion of the length of the grasper parallel to the longitudinal axis. The filament may form a loop at the second end. The filament loop may include a first end and a second end of a wire fixed within the wedge. The hinge may extend about a plane substantially perpendicular to the loop of the filament. An alignment member may be at the second end of the grasper. The filament may extend through a channel of the alignment member. The alignment member may be configured to align the grasper with a lumen of an instrument sheath.

In various embodiments, a tissue clip system may include an elongate tether member. The system may include a first tissue clip. The system may include a second tissue clip. Each tissue clip may be disposed at an opposite end of the elongate tether member. A tissue clip may comprise a grasper including jaws at a first end of the grasper. A spring portion may be at a second end. The grasper may extend a length from the first end to the second end along a longitudinal axis. The spring portion may be configured to bias the jaws toward each other. In some embodiments, a wedge may be slidably disposed between the jaws such that an apex of the wedge is oriented toward the spring portion. A filament may be coupled to the wedge. A deployment catheter having an engagement end may be slidably disposed within a lumen of an instrument sheath and configured to engage the filament. In alternate embodiments, a spring actuator and the spring portion are movable substantially axially relative to each other to cause the spring portion to move the jaws apart. The spring portion may have one or more ramps engaging the spring actuator to cause the jaws to move apart. The spring actuator may be a capsule or cylinder or collar.

In various embodiments, a retainer may be disposed within the second end of the grasper. A hinge may be at least partially extending through the retainer. The retainer may be rotatable about the hinge. A first end of the hinge may be disposed within the retainer. A second end of the hinge may include an attachment member configured to attach to a tether member. A tab may be disposed on the wedge. The tab may be slidably disposed within a slot that extends along at least a portion of the length of the grasper. Each tissue clip may include an alignment member at the second end of the grasper. A first end of the filament may be connected to the wedge. The filament may extend through a channel of the spring portion of the grasper.

In various embodiments, a method of clipping tissue may include delivering a first tissue clip. The method may include delivering a second tissue clip. Each tissue clip may be disposed at an opposite end of an elongate tether member. A tissue clip may be delivered to a first target location of the tissue in a body lumen. Each tissue clip may comprise a grasper including jaws at a first end. A spring portion may be at a second end. The grasper may extend a length from the first end to the second end along a longitudinal axis. The spring portion may be configured to bias the jaws toward each other. In some embodiments, a wedge may be slidably disposed between the jaws such that an apex of the wedge is oriented toward the spring portion. A filament may be coupled to the wedge. A deployment catheter wedge may engage the filament of the first tissue clip to open and engage the jaws of the grasper of first clip at the first target location of the tissue in the body lumen. In alternate embodiments, a spring actuator and the spring portion are moved substantially axially relative to each other to cause the spring portion to move the jaws apart. The spring portion may have one or more ramps engaging the spring actuator to cause the jaws to move apart. The spring actuator may be a capsule or cylinder or collar.

In various embodiments, the filament of the second tissue clip may be engaged to open and engage the jaws of the grasper second clip at a second target location of tissue in the body lumen, such that the tissue may be held in a selected position. The second tissue clip may be repositioned from the second target location of tissue in the body lumen to a third target location of tissue in the body lumen. A distance between the first tissue clip and the second portion may be longer than a distance between the first tissue clip and the first portion. The method may include engaging an end of the filament of the second tissue clip with a delivery catheter and removing the second tissue clip, the elongate tether member, and the first tissue clip engaging the first target location of the tissue from a patient. A longitudinal axis of the first tissue clip may be aligned with a lumen of an instrument sheath of the delivery catheter.

BRIEF DESCRIPTION OF THE DRAWINGS

Non-limiting examples of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment of the disclosure shown where illustration is not necessary to allow those of skill in the art to understand the disclosure. In the figures:

FIG. 1A illustrates an isometric view of a tissue retraction/traction system including an elongate tether and two tissue clips, in accordance with an embodiment of the present disclosure.

FIG. 2B illustrates a partial cross-sectional view of the deployment catheter of FIG. 2A including a tissue clip in a closed configuration, in accordance with an embodiment of the present disclosure.

FIG. 2C illustrates a partial cross-sectional view of the deployment catheter of FIGS. 2A and 2B including the tissue clip of FIG. 2B in an open configuration.

FIG. 2D illustrates a partial cross-sectional view of the deployment catheter of FIGS. 2A-2C including the tissue clip of FIGS. 2B and 2C and also including an elongate tether and an additional tissue clip, in accordance with an embodiment of the present disclosure.

FIG. 3A illustrates a cross-sectional view of a tissue clip, in accordance with an embodiment of the present disclosure.

FIG. 3B illustrates a cross-sectional view of the tissue clip of FIG. 3A.

FIG. 5A illustrates an isometric view of an alternate tissue clip, in accordance with an embodiment of the present disclosure.

FIG. 5B is a cross-sectional view of the tissue clip of FIG. 5A.

FIG. 5C illustrates a section of a deployment catheter including a tissue clip as in FIGS. 5A and 5B in a closed configuration, in accordance with an embodiment of the present disclosure.

FIG. 5D illustrates a section view of the deployment catheter of FIG. 5C including an isometric view of the tissue clip of FIGS. 5A and 5B in an open configuration.

Figure 1B:
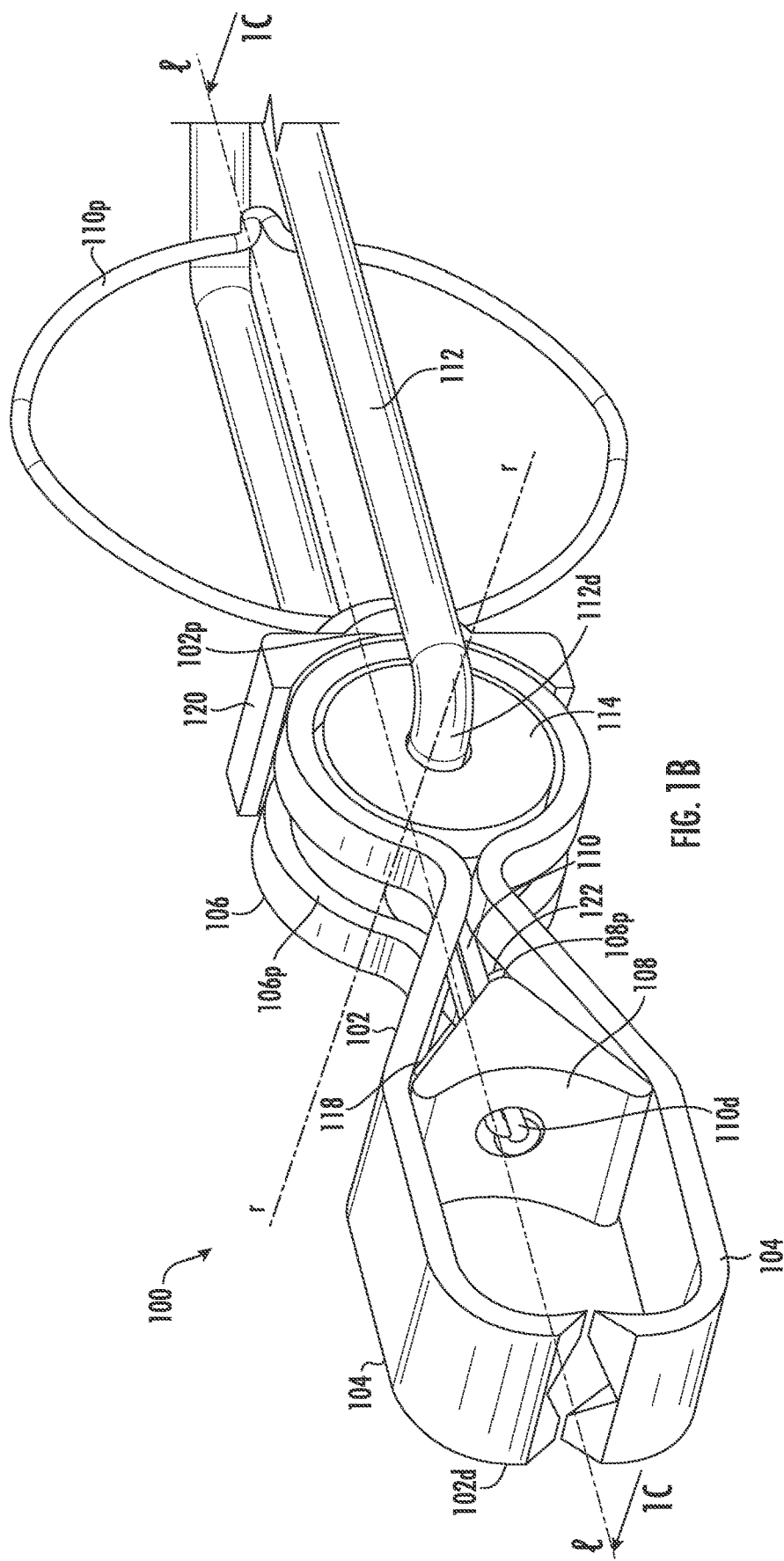
FIG. 1B illustrates an isometric view of one of the clips of FIG. 1A.

It is noted that the drawings are intended to depict only typical or exemplary embodiments of the disclosure. Accordingly, the drawings should not be considered as limiting the scope of the disclosure. The disclosure will now be described in greater detail with reference to the accompanying drawings.

DETAILED DESCRIPTION

Various embodiments according to the present disclosure are described below. As used herein, "proximal end" refers to the end of a device that lies closest to the medical professional along the device when introducing the device into a patient, and "distal end" refers to the end of a device or object that lies furthest from the medical professional along the device during implantation, positioning, or delivery.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

The detailed description should be read with reference to the drawings, which are not necessarily to scale, depict illustrative embodiments and are not intended to limit the scope of the invention.

A number of medical procedures, including intravascular procedures, procedures along the digestive and/or biliary tract, thoracic procedures, etc. utilize medical devices to access tissue intended for removal (e.g., "target tissue") within the body. For example, in some current medical procedures (e.g., ESD, Peroral Endoscopic Myotomy (POEM), cholecystectomy, Video-Assisted Thoracoscopic Surgery (VATS)), physicians may utilize an endoscope or similar medical device to access and remove diseased lesions. Further, as part of the procedure, the physician may utilize an endoscope capable of both accessing the target tissue site while also permitting a resecting device to be deployed therethrough to resect target tissue. Additionally, in some instances, an endoscope may incorporate features which assist the physician in visualizing and performing the tissue dissection/resection procedure. For example, some endoscopes may include a light and/or camera designed to illuminate and/or visualize the body lumen as the endoscope is navigated and positioned adjacent to the target tissue site. Additionally, some endoscopes may also include a lumen (e.g., a working channel) through which a resecting device, grasping member, or other accessory devices may be deployed and utilized. Additional visualization methods may be alternatively or additionally employed, e.g., fluoroscopy.

While physicians are becoming more proficient at resecting diseased lesions from within the body (e.g., within the digestive tract, abdominal cavity, thoracic cavity, etc.), present retraction/traction methods continue to be inefficient and frustrating to the physician. For example, in some instances poor visualization and poor ability to engage and manipulate and traction tissue may result in a prolonged tissue dissection procedure. One aspect of ESD that may be difficult is the positioning and maneuvering (e.g., retraction) of a resected tissue flap during and after cutting. In ESD procedures, physicians may use devices to provide a means of tissue traction/retraction. Such procedures may include multiple device exchanges and extended procedure times. Often when traction/retraction is provided by an endoscopic cap, a physician's view may be obstructed and cause the physician to lose his or her bearings in relation to the target tissue margins. In another example, the target tissue that the physician is attempting to dissect may obstruct the pathway of the tools that the physician is using during the procedure.

Other clip devices may be difficult to open, close, and/or position, because the clip devices may require gripping along a specific angle or plane. Operating such devices may be difficult for a medical professional because of the viewing angle, devices or anatomies blocking the field of view, size of the operating tools, or strict angles of proper engagement with respect to the devices, as examples. Attempts to manipulate tissue traction devices at various angles may fail to control the device properly, cause procedural errors, delay, or frustrate the medical professional.

Disclosed herein are medical devices such as tissue clip devices and delivery systems that are designed to efficiently engage, lift, and/or retract the target tissue. Some other example devices which may complement devices and methods of the present disclosure are disclosed in U.S. Patent Application Publication number 2018/0263614, filed Mar. 19, 2018, and titled, "Tissue Retraction Device and Delivery System"; U.S. Patent Application Publication 2020/0360005, filed on May 13, 2020, and titled "Tissue Traction Bands And Methods Of Use Thereof"; U.S. Patent Application Publication 2020/0360006, filed on May 13, 2020, and titled "Tissue Traction Bands And Methods For Tissue Traction"; U.S. Patent Application Publication 2020/0390446, filed on May 13, 2020, and titled "Tether Traction Systems And Methods Of Use Thereof"; U.S. Patent Application Publication number 2020/0129181, filed Oct. 30, 2019, and titled "Clip Devices, Systems, and Methods for Engaging Tissue"; and U.S. Pat. No. 8,062,311, issued Nov. 22, 2011, and titled "Endoscopic Hemostatic Clipping Apparatus", each of which is herein incorporated by reference in its entirety for all purposes.

Figure 1C:
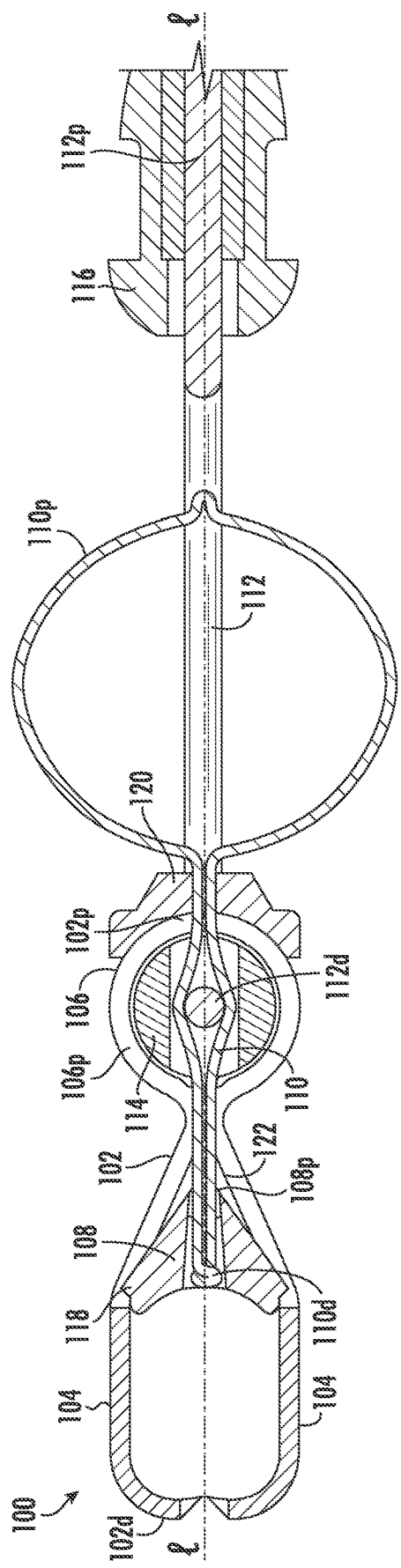
FIG. 1C illustrates a cross-sectional view of the clip of FIG. 1B.

Referring to FIG. 1A, an isometric view of a tissue retraction/traction (such terms being used in the alternative/interchangeably, or simply referenced as "traction" for the sake of simplicity and without intent to limit) device 100 of the present disclosure may include a traction band 110 (e.g., elastic band, tether, stretchable elongate member, etc.) system is illustrated according to an embodiment of the present disclosure, which includes an elongate tether member 150 with a first and second tissue clip 100 each disposed at opposite ends of the elongate tether member 150 (a first clip at one end and a second clip at the opposite end of the elongate tether). The tissue clips 100 are each fixed to the elongate tether member 150 by an attachment member 116. Each clip 100, as further illustrated by the isometric view of FIG. 1B and the cross-sectional view of FIG. 1C, includes a grasper 102. The grasper 102 has two jaws 104 at a first end 102d of the grasper 102 and a spring portion 106 at a second end 102p of the grasper 102. A longitudinal axis $\ell$ extends along the length of the grasper 102 through the first end 102d and the second end 102p. The spring portion 106 is configured to bias the jaws 104 toward each other in the closed configuration as illustrated in FIGS. 1A-1C. A wedge 108 is slidably disposed between the jaws 104 such that an apex 108p of the wedge is oriented toward the spring portion 106 along the longitudinal axis $\ell$. The wedge 108 may be configured to slide toward the second end 102p of the grasper along the longitudinal axis $\ell$ to open the jaws 104 such that the clip 100 is in the open configuration (e.g., as illustrated in FIG. 2C, discussed below). A tab 118 may be disposed on and fixedly coupled to each of the inclined planes of the wedge 108, with the tab slidable within a slot 122 extending along a portion of the grasper 102 along the longitudinal axis $\ell$. The tab 118 extends partially into and along the slot 122 such that the wedge 108 cannot readily be dislodged from between the jaws 104 of the grasper 102. A filament 110 is connected to the wedge 108 at a first end 110d of the filament. The filament 110 extends through a channel 106p of the spring portion 106 of the grasper 102 to a second end 110p of the filament 110. The second end 110p of the filament 110 forms a loop in a plane that extends substantially through and radially away from the longitudinal axis $\ell$. The loop may be fixed in position with respect to wedge 108, i.e., not rotatable about the longitudinal axis $\ell$, or the loop may be rotatable. The loop may be formed from the material of the filament 110 and may be other shapes, as discussed below. At least a portion of the filament 110 may be formed of a shape memory material (e.g., nitinol), such that the second end 110p may repeatably re-form into a set shape (e.g., loop-form) for manipulation with an accessory tool to articulate or actuate the jaws 104 of the grasper 102. Because the first end 110d of the filament 110 is attached to the wedge 108, the loop at the second end 110p may be moved away from the grasper 104 generally along the longitudinal axis $\ell$ to also move the wedge 108 toward the second end 102p of the grasper 102 to open the jaws 104 such that the clip 100 is in the open configuration.

A retainer 114 is disposed within the second end 102p of the grasper 102. In some embodiments, a retainer may be one piece with channel(s) for a filament to extend through. In other embodiments a retainer may be two pieces with a filament extending between the two pieces of the retainer. A hinge 112 is disposed through the retainer 114, and the retainer 114 is rotatable about the hinge 112 along an axis ℓ, which extends through the retainer 114 and perpendicularly to the longitudinal axis 13. The first end 112d of the hinge 112 extends through the retainer 114 and the second end 112p of the hinge 112 is attached to the attachment member 116. An alignment member 120 is adjacent the second end 102p of the grasper 102. The filament 110 extends through the alignment member 120 such that the alignment member 120 is bounded substantially along the longitudinal axis ℓ on one side by the grasper 102 and is bounded on another side by the second end 110p of the filament 110 that is the loop. The alignment member 120 may assist with operating the jaws 104 and general manipulation of the clip 100 (e.g., as will be discussed with reference to FIGS. 2B-3B below).

Figure 2A:
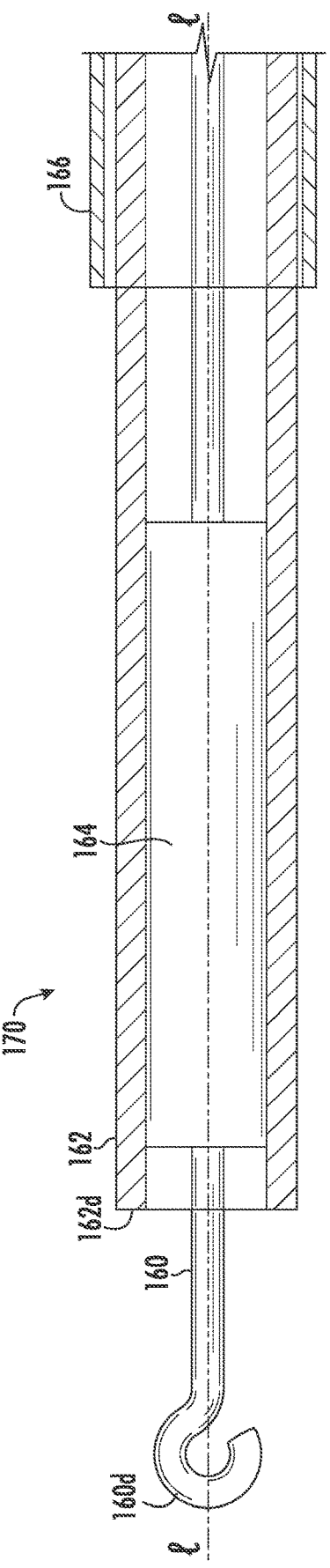
FIG. 2A illustrates a right partial cross-sectional view of a deployment catheter having an engagement end, in accordance with an embodiment of the present disclosure.

Referring to FIG. 2A, a right view of a deployment catheter 170 is illustrated as part of a tissue retraction/traction system according to an embodiment of the present disclosure. The deployment catheter 170 includes an engagement portion 160d of an instrument 160, an instrument sheath 162, and an optional outer sheath 166. In some embodiments, the deployment catheter 170, with or without the tissue clips 100 and a tether member 150 engaged, may be manipulated into and out of a working channel of an endoscope without the catheter having an outer sheath 166. Use of the outer sheath 166 may advantageous, e.g., to protect against any edges of the tissue retraction system from catching, scratching, or otherwise adversely interacting with the working channel of the endoscope. The engagement portion 160d of the instrument 160 may be a hook, but the engagement portion 160d may be an alternative shape or manner of connection that is configured to engage a filament 110 (e.g., the loop of the proximal end 110p of a filament 110), such as, e.g., a grasper, a clamp, a basket, a clip, a gripper, a magnet, an adhesive, or the like. The deployment catheter 170 may be deployable through a working channel of a scope with or without the outer sheath 166. The instrument 160 is slidably disposed within the instrument sheath 162. The instrument sheath 162 and the instrument 160 extend into the outer sheath 166, which may be an introducer catheter. The instrument 160 includes a centering member 164 about the instrument 160 that extends along the longitudinal axis ℓ. The centering member 164 has an outer diameter substantially matching an internal diameter of a lumen of the instrument sheath 162 such that the centering member 164 and the medical instrument 160 extending therethrough are substantially centered within the lumen of the instrument sheath 162. In some embodiments, the outer diameter of the centering member 164 may be smaller than the internal diameter of the lumen of the instrument sheath 162 to allow the centering member 164 to slide along the sheath 162.

FIGS. 2B and 2C illustrate right partial cross-sectional views of the system of FIG. 2A including a tissue clip 100. The engagement portion 160d of the medical instrument 160 is engaged with the loop of the second end 110p of the filament 110. The instrument 160 is orienting the clip 100 substantially along the longitudinal axis ℓ by maintaining the second end 110p of the filament 110 within the sheath 162 such that the alignment member 120 at least partially seats within a distal end 162d of the sheath 162. The alignment member 120 has a first portion 120d that has an outer diameter that is wider than an inner diameter of the lumen of the sheath 162, and the alignment member 120 has a second portion 120p (e.g., in the shape of a frustum) that has a maximum outer diameter that is smaller than the inner diameter of the lumen of the sheath 162. When the instrument 160 moves the alignment member 120 toward the distal end 162d of the sheath 162 via the filament 110, the second portion 120p enters the lumen of the distal end 162d of the sheath 162. The frustum shape of the second portion 120p may engage the inside edge of the distal end 162d so that the alignment member 120 is oriented in a manner such that a central axis through the center of the alignment member 120 is substantially aligned with the longitudinal axis ℓ. The first portion 120d of the alignment member 120 has an outer diameter that does not fit within the lumen of the distal end 162d. A surface of the first portion 120d that extends about the second portion 120p is flat such that when the instrument 160 moves the first portion 120d of the alignment member 120 into contact with the distal end 162d of the sheath 162, the majority of the inner edge of the distal end 162d is in substantial contact with the alignment member 120, fixing the alignment member 120, the grasper 102, and the sheath 162 with respect to the filament 110. In this position of FIG. 2B, the alignment member 120 and the clip 100 are oriented (i.e., centered) substantially along the longitudinal axis ℓ. Maintaining the position of FIG. 2B may require some proximal tension (e.g., pulling) on the filament. The clip 100 is illustrated as aligned with the longitudinal axis ℓ in the closed configuration in FIG. 2B. From the aligned and closed configuration, the second end 110p of the filament 110 may be further pulled by the instrument 160 within the sheath 162 in a direction away from the distal end 162d of the sheath so that the clip 100 transitions from the closed configuration to the open configuration, as illustrated in FIG. 2C. In the open configuration, the jaws 104 are moved farther apart from each other than in the closed configuration. As the instrument 160 pulls on the second end 110p, the first portion 120d of the alignment member 120 abuts the distal end 162d of the sheath 162 and fixes the grasper 102 with respect to the filament 110. Applying further tension on the filament 110 from the instrument 160 moves the wedge 108 along the longitudinal axis ℓ toward the retainer 114 and forces the jaws 104 apart from each other into the open configuration. The retainer 114 and grasper 102 freely rotate about the portion of the hinge 112 extending through the retainer 114 (i.e., axis r through the center of the hinge 112) during operation of the clip 100 so that the jaws 104 may be oriented toward a target tissue for engagement without hinderance from the hinge 112. Hinge 112 is illustrated in phantom lines along the longitudinal axis ℓ and is illustrated in solid lines in another position about the retainer 114. The grasper 102 may freely rotate about the hinge 112 while in the closed configuration or in the open configuration. FIG. 2D illustrates a partial cross-sectional view of the systems of FIGS. 2A-2C with the instrument 160, the sheath 162, and the clips 100 connected by attachment members 116 to an elongate tether member 150 within the outer sheath 166. The clips 100 and elongate tether member 150 (other than the second end 110p of a filament 110 of the proximal clip 100) are outside of and distal to the sheath 162. The filament 110 of the proximal clip 100 is positioned proximally to the grasper 102 such that the instrument 160 may engage the filament 110. Tissue retraction/traction systems herein may be preloaded, e.g., substantially as illustrated in FIG. 2D for procedures such as those described with respect to FIGS. 5A-5F. Because the filament 110 of the proximal clip 100 is engaged by the medical instrument 160 before the clips 100 are deployed into a patient, the proximal clip 100 will immediately be ready for use, reducing procedure time and likelihood of error when compared to other systems that do not have a clip engaged in the preloaded state before deployment.

With reference to FIG. 3A, a tissue clip 300 according to an embodiment of the present disclosure is illustrated, which is similar to the clips 100 described in FIGS. 1A-2D. However, first end 309 and second end 311 of a wire of the filament 310 extend through separate lumens of the clip 300 rather than through a shared lumen. The tissue clip 300 includes a first lumen 305 of a wedge 308 and a second lumen 307 of the wedge 308 that are both parallel to a longitudinal axis ℓ that extends through the clip 300. A first lumen 313 of a retainer 314 is substantially aligned with the first lumen 305 of the wedge 308 and a second lumen 315 of the retainer 314 is substantially aligned with the second lumen 307 of the wedge 308. A first lumen 319 of an alignment member 320 is substantially aligned with the first lumen 313 of the retainer 314 and a second lumen 321 of alignment member 320 is substantially aligned with the second lumen 315 of the retainer 314. The first end 309 of the wire of the filament 310 extends from a first end 310d of the filament 310, at the first lumen 305 of the wedge 308, through the first lumen 313 of the retainer 314, and through the first lumen 319 of the alignment member 320. The filament 310 may form a loop at an opposite second end 310p, so that the second end 311 of the wire of the filament 310 extends from the second lumen 307 of the wedge 308, through the second lumen 315 of the retainer 314, and through the second lumen 321 of the alignment member 320. The ends 309, 311 are fixed with respect to the wedge 308 and may move through the first and second lumens 313, 315 of the retainer 314. The spaced apart ends 309, 311 of the wire of the filament 310 that are offset from the longitudinal axis ℓ may require less tension force on the second end 310p of the filament 310 to slide the wedge 308 to the open configuration of the grasper, as compared to the clips 100 of FIGS. 1A-2D, because the wire of the filament 310 does not need to overcome a frictional force of the hinge 312 in the center of the retainer 314, intersecting the longitudinal axis ℓ. In FIG. 3B, which illustrates a cross-sectional view of the tissue clip 300 of FIG. 3A, without an alignment member, the first end 309 of the wire of the filament 310 extends from the first lumen 305 of the wedge 308, through the first lumen 313 of the retainer 314, and the second end 311 of the wire of the filament 310 extends from the second lumen 307 of the wedge 308 through the second lumen 315 of the retainer 314. As the grasper 302 is pulled toward the sheath 362 by an instrument 160 via the filament 310, the grasper 302 may not be aligned with the longitudinal axis ℓ. If the grasper 302 is not aligned with the longitudinal axis ℓ, tension in the wire of the filament 310 from a pulling force within the sheath 362 may create a moment about the hinge 312 that causes one of the ends 309, 311 of the wire of the filament 310 to rotate the grasper 302 about the hinge 312 at the distal end 362d of the sheath 362. For example, if the grasper 302 is not aligned with the longitudinal axis ℓ, such that the jaws 304 are below the longitudinal axis ℓ in FIG. 3B, pulling on the filament 310 in the sheath 362 would cause the first end 309 of the wire of the filament 310 to create a moment within the first lumen 313 about the hinge 312 such that the first and second lumens 313, 315 of the retainer 314 would orient parallel to the longitudinal axis ℓ.

Figure 4A:
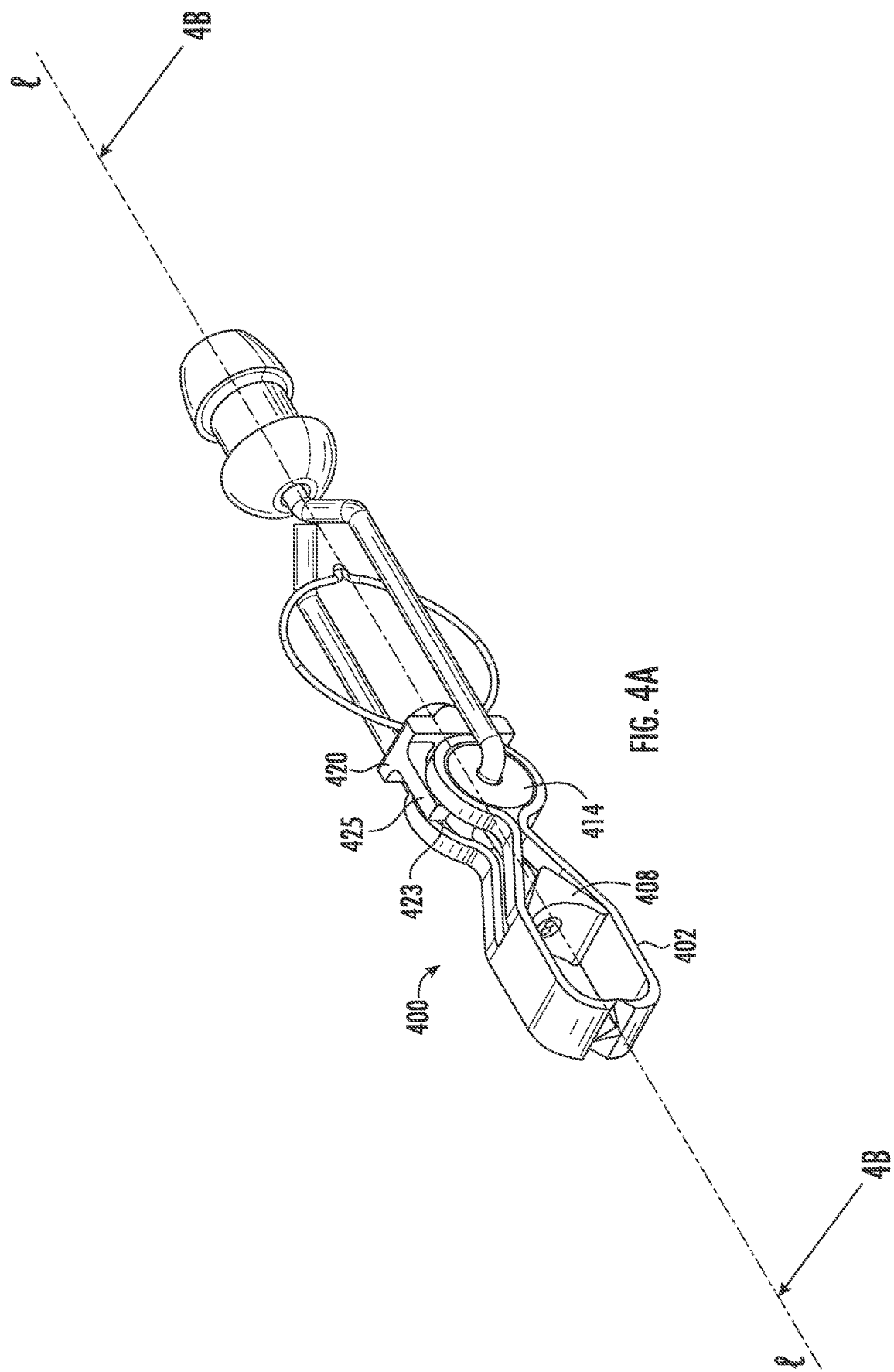
FIG. 4A illustrates an isometric view of a tissue clip, in accordance with an embodiment of the present disclosure.
Figure 4B:
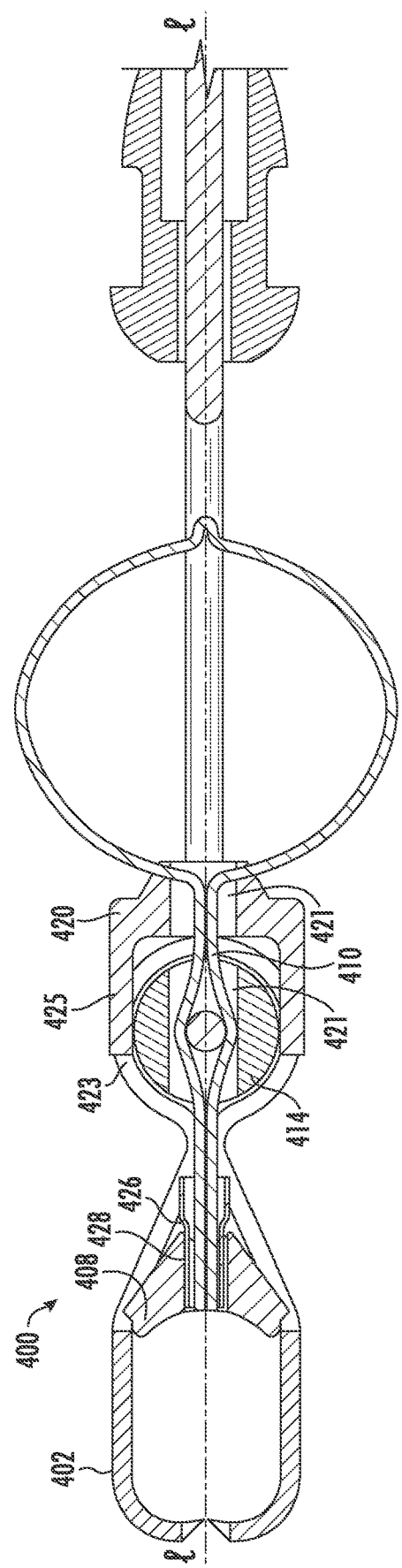
FIG. 4B. illustrates a cross-sectional view of the clip of FIG. 4A.

With reference to FIGS. 4A and 4B, a tissue clip 400 according to an embodiment of the present disclosure is illustrated, which is similar to the clips 100 described in FIGS. 1A-2D, but has an alignment member 420 fixed to a retainer 414 via extensions 425. With the alignment member 420 fixed to the retainer 414, a filament 410 may better align with the longitudinal axis 13 when compared to an embodiment with the alignment member 420 not fixed to the retainer 414. For example, the alignment member 420 may be fixed to the retainer 422, and a lumen 421 may extend through both the alignment member 420 and the retainer 414, so that the filament 410 may extend straight through the alignment member 420 and the retainer 414 via the lumen 421, as depicted in FIG. 4B. The extensions 425 are disposed in a slot 423 of the grasper 402. A ferrule 426 is deformed (e.g., crimped) about a first end of the filament 410 of the clip 400, extended into a lumen 428 of a wedge 408, and the ferrule 426 is attached (e.g., press fit or welded) to the wedge 408. The ferrule 426 may provide an assembly that is easier to manufacture when compared to welding the filament 410 if the materials are dissimilar metals.

Yet another tissue clip 500 formed in accordance with principles of the present disclosure is illustrated in FIGS. 5A-D. Referring to FIG. 5A, an isometric view of a tissue clip 500 is illustrated according to an embodiment of the present disclosure. The grasper 502 of the tissue clip 500 has two jaws 504 at a first end 502d of the grasper 502 and a spring portion 506 proximal to the first end 502d of the grasper 502, at an intermediate position 502i along the grasper 502. The spring portion 506 may be more readily viewed with reference to the cross-sectional view of FIG. 5B. A longitudinal axis ℓ extends along the length of the grasper 502 through the first end 502d and the second end 502p. The spring portion 506 is configured to maintain the jaws 504 in a closed configuration, as illustrated in FIGS. 5A-5C, until the spring portion 506 is actuated to bias the jaws 504 apart. Actuation of the jaws 504 may be achieved in any of a variety of manners to separate the jaws 504 (e.g., such that tissue may be located between the jaws 504 and the jaws 504 brought together again to clip the tissue therebetween). For instance, the spring portion 506 may be shaped and configured to engage or be engaged by another element, such as a spring actuator 508, which actuates the spring portion 506. In the embodiments of FIGS. 5A-5D, the spring actuator 508 and the spring portion 506 are configured to move substantially axially relative to each other to cause the spring portion 506 to move the jaws 504 apart. In the illustrated embodiment, the spring portion 506 has two opposed ramps 506a, 506b which engage a spring actuator 508 in the form of capsule or cylinder or collar (hereinafter "capsule" for the sake of convenience and without intent to limit). In the embodiment of FIGS. 5A-5D, a snare 510p is provided on a proximal end of the clip 500, such as being formed by proximal ends of the wire or other material forming the grasper 502, or by otherwise being coupled to the proximal end of the grasper 502. The snare 510p may be pulled proximally by an instrument such as an instrument 160 as described above, and as illustrated in FIGS. 5C and 5D in use with the clip 500. More particularly, the engagement portion 160d of the instrument 160 may engage the snare 510p to move the grasper 502 and the spring actuator 508 proximally. Once the proximal end 508p of the spring actuator 508 abuts the distal end 162d of the instrument sheath 162 (such as shown in FIG. 5D), or otherwise does not advance further proximally, the ramps 506a, 506b of the spring portion 506 continue to move toward the distal end 508d of the spring actuator 508 as the instrument 160 is moved proximally. As the ramps 506a, 506b continue to move proximally, they engage the distal end 508d of the spring actuator 508, and advance proximally within the spring actuator 508 to cause the ramps 506a, 506b to be increasing drawn closer together, thereby causing the jaws 504 (given the configuration in which the jaws 504 are coupled or formed with the ramps 506a, 506b) to move apart. The clip 500 is thereby opened.

Figure 6:
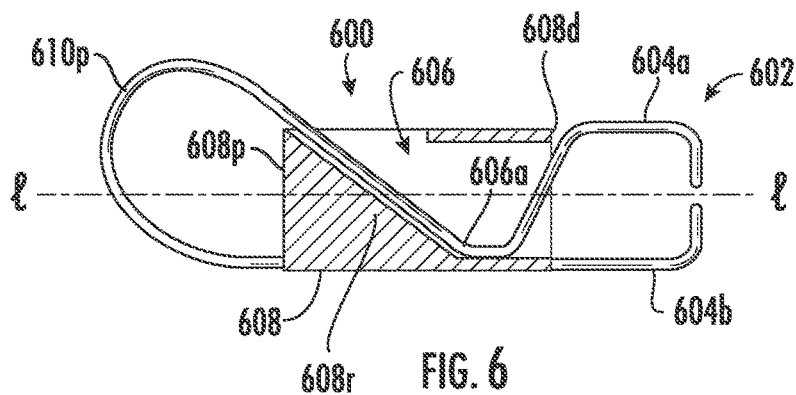
FIG. 6 illustrates a cross-sectional view of a tissue clip similar to that of FIGS. 5A-5D with a modified structure for actuating the clip jaws.

A tissue clip 600 similar to the clip illustrated in FIGS. 5A-5D, but with a modified structure for actuating the clip jaws to move with respect to each other, is illustrated in FIG. 6. As illustrated, the spring portion 606 has only one ramp 606a which rides along a spring actuator ramp 608r in the spring actuator 608 as the grasper 602 is moved proximally (such as by being engaged and moved proximally by an instrument 160 as previously described). As the spring ramp 606a moves proximally over the spring actuator ramp 608r towards the proximal end 608p of the spring actuator 608, the upper jaw 604a of the grasper 602 is moved away from the lower jaw 604b to open the clip 600. In one embodiment, the proximal end of the lower jaw 604b may be coupled (e.g., fixed to) the distal end 608d of the spring actuator 608. A snare 610p may be coupled to the proximal end of the clip, such as being formed by a proximal end of the wire or other material forming the upper jaw 604a and the spring ramp 606a, or by otherwise being coupled to the proximal end of the grasper 602. An end of the snare 610 may be coupled (e.g., fixed to) the proximal end 608p of the spring actuator 608, such as for stability.

Figure 7:
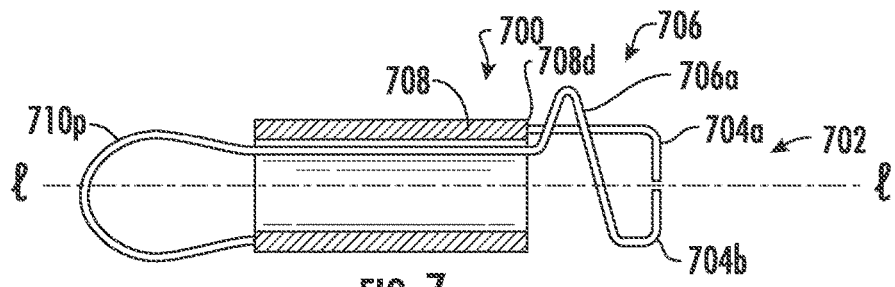
FIG. 7 illustrates a cross-sectional view of a tissue clip similar to that of FIGS. 5A-5D and 6 with a modified structure for actuating the clip jaws.

Yet another tissue clip 700 is illustrated in FIG. 7. Similar to the tissue clip 600 of FIG. 6, the tissue clip 700 has a spring portion 706 with only one spring ramp 706a. As the grasper 702 is moved proximally relative to the spring actuator 708 (such as by being engaged and moved proximally by an instrument 160, such as by engagement of an instrument engagement portion 160d with a snare 710p on the proximal end of the grasper 702, in a manner as previously described), the spring actuator 708 may be moved into abutment with a distal end 162d of the instrument sheath 162 as described with reference to the clip 500 and as illustrated in FIGS. 5C and 5D. Once the spring actuator 708 abuts the distal end 162d of the instrument sheath 162 (in a similar manner as shown in FIG. 5D), or otherwise does not advance further proximally, the ramp 706a continues to move toward the proximal end 708p of the spring actuator 708 as the instrument 160 is moved proximally. As the ramp 706a continues to move proximally, it engages the distal end 708d of the spring actuator 708, and advances proximally within the spring actuator 708 to cause the ramp 706a to be increasing drawn downward, thereby causing the lower jaw 704b (given the configuration in which the jaw 704b is coupled or formed with the ramp 706a) to move downwardly and away from the upper jaw 704a. The clip 700 is thereby opened.

Figure 8A:
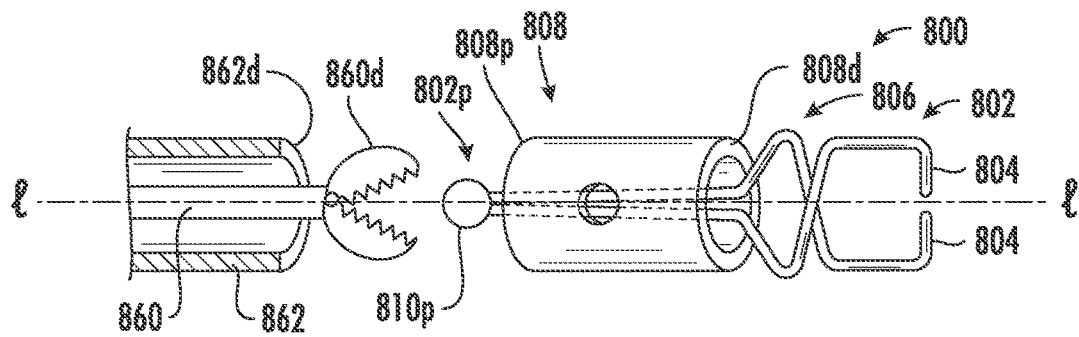
FIGS. 8A and 8B illustrate an alternative deployment catheter and instrument with a modified clip in accordance with an embodiment of the present disclosure.
Figure 8B:
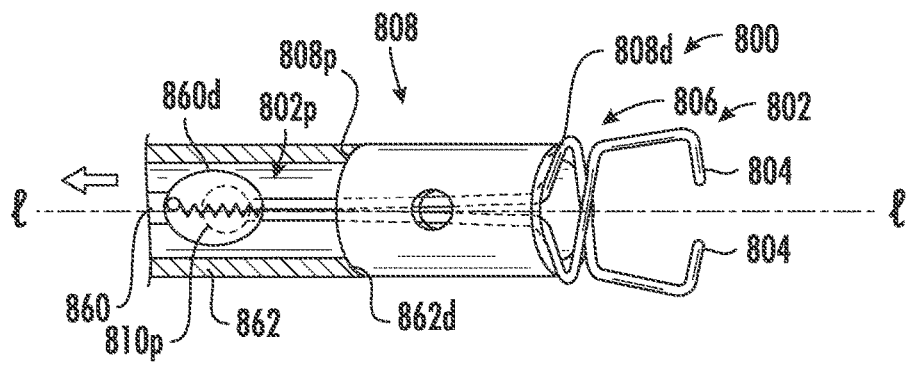

As described above, in the above-described embodiments illustrated in FIGS. 1A-1C, 2A-2D, 3A-3B, 4A-4B, 5A-5D, 6, and 7, a clip may be provided with a filament or snare or other element through which an engagement portion of an instrument is passed and moved proximally to move the clip proximally to actuate the grasper thereof to open. It will be appreciated that alternatives are within the scope of the present disclosure. For instance, instead of an engagement portion of an instrument passing through a proximal portion or element of a clip or grasper, an engagement portion of an instrument may be engaged over a portion or element of a clip or grasper. In one embodiment, illustrated in FIGS. 8A and 8B, a proximal end 102p of a grasper 802 of a clip 800 may be provided with an engagement element 810p over which an engagement portion 860d of an instrument 860 is engaged to actuate the grasper 802 to open. The engagement portion 860d may be in the form of a grasper, a clamp, a basket, a clip, a gripper, a magnet, an adhesive, or the like which engages with (e.g., is fitted over) a substantially three-dimensional (solid or hollow) engagement element 810p such as a sphere/ball or polyhedron. The instrument 860 is moved proximally to move the engagement portion 860d thereof along with the engagement element 810p, thereby proximally moving the grasper 802 to actuate the jaws 804 to open. Actuation of the jaws 804 of a grasper 802 may be achieved as described above depending on the configuration of the jaws. In the embodiment of FIGS. 8A and 8B, a grasper 802 similar to the grasper 502 of the embodiments illustrated in FIGS. 5A-5D is shown for the sake of illustration (and without intent to limit). It will be appreciated that the engagement element 810p need not be limited to use with the particular configuration of a grasper and jaws and ramps as illustrated. As may be appreciated, proximal movement of the instrument 860 moves the instrument engagement portion 860d and the clip engagement element 810p to move the clip 800 along with the spring actuator 808 proximally. Once the spring actuator 808 abuts the distal end 862d of the instrument sheath 862 (such as shown in FIG. 8B), or otherwise does not advance further proximally, the ramps 806a, 806b of the spring portion 806 continue to move toward the proximal end 808p of the spring actuator 808. As the ramps 806a, 806b continue to move proximally, they engage the distal end 808d of the spring actuator 808, and advance proximally within the spring actuator 808 to cause the ramps 806a, 806b to be increasing drawn closer together, thereby causing the jaws 804 to move apart. The clip 800 is thereby opened. It will be appreciated that the other configurations of jaws shown and described herein may be used instead of the jaws depicted in FIGS. 8A and 8B in connection with the instrument engagement portion 860d and grasper engagement element 810p illustrated therein.

In the clip and grasper embodiments described thus far, the grasper jaws have been actuated into an open position generally by relative advancement of an instrument and grasper. For instance, the actuation may be generally described as being achieved by proximal advancement of an instrument to advance the grasper proximally into engagement with another element to actuate the grasper jaws to open, such as by engaging a spring portion of the grasper with a spring actuator to open the grasper jaws. Alternative grasper jaw actuation mechanism and methods are within the scope of the present disclosure as well.

Figure 9A:
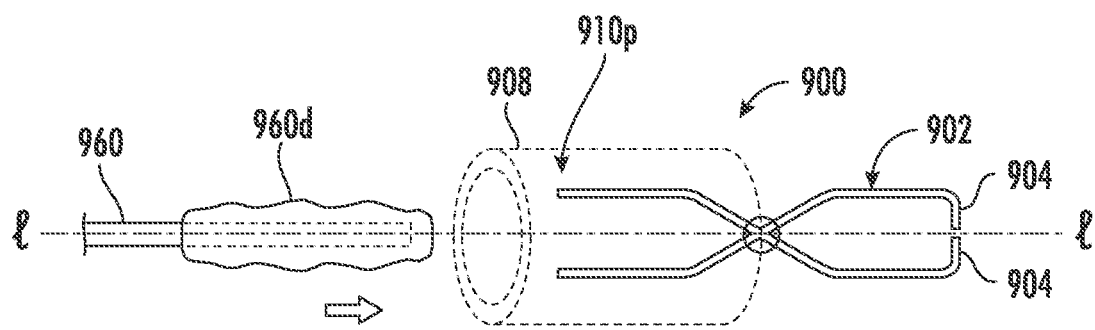
FIGS. 9A-9C illustrate an alternative clip and deployment instrument in accordance with an embodiment of the present disclosure.
Figure 9B:
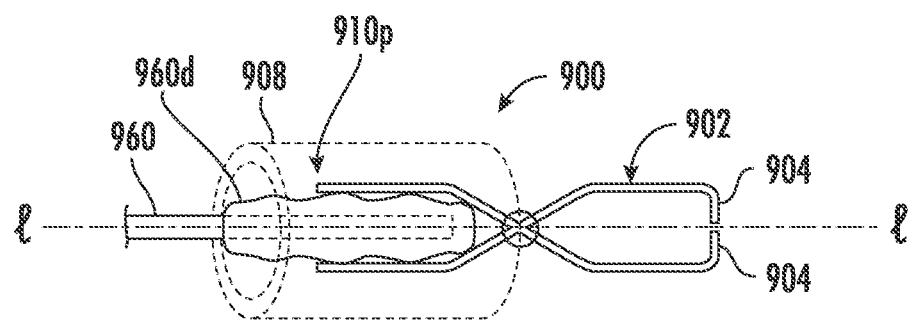
Figure 9C:
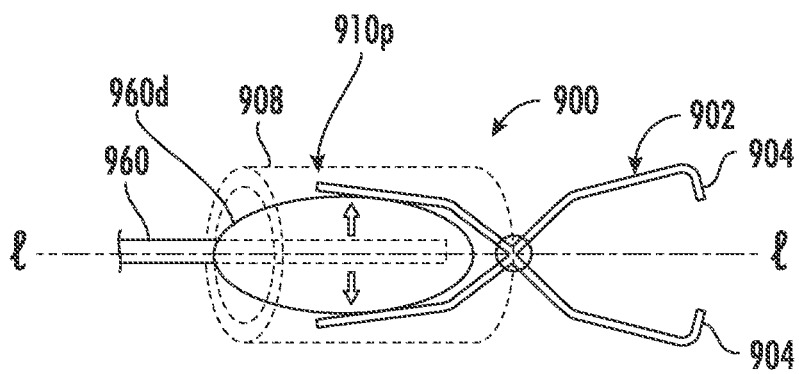

For instance, with reference to FIGS. 9A-9C, actuation of a grasper 902 of a clip 900 may be achieved by relative radial movement/engagement between a proximal engagement element 910p of the grasper 902 with an engagement portion 960d of an instrument 960. In the illustrated example of FIGS. 9A-9C, the instrument engagement portion 960d is in the form of an expandable element, such as an inflatable balloon, inserted into an engagement element or end 910p of the grasper 902. As the instrument engagement portion 960d expands, the jaws 904 of the grasper 902 are drawn apart (given the configuration in which the jaws 904 are coupled with the engagement element 910p). The clip 900 is thereby opened.

Returning to discussion of a tissue retraction/traction system in which a clip is disposed at ends of an elongate tether member, in various embodiments, an elongate tether member may be a rigid member or an elastic member, or combinations thereof. An elongate tether member having a length may stretch to an additional length that is about 50% to about 500% longer than the original length. An elongate tether member may comprise rubber, silicone, polymer, metal, alloy, thermoplastic elastomer, liquid silicone rubber, natural rubber, or the like. An elongate tether member may be tubular or solid. Attachment members may be permanently or removably fixed to an elongate tether member in various ways such as snap-fitted, welded, tied, glued, linked, or the like. An elongate tether member may include depressions and/or apertures for a medical instrument to engage.

In various embodiments, a first end of a filament may be connected to a wedge in various ways. For example, the filament may be welded, soldered, brazed, bonded, glued, adhered, or otherwise fixedly attached, to the wedge. The filament may be knotted or crimped such that it has a wider outer diameter than an inner diameter of a lumen extending through the wedge. The filament may be press-fit into a wedge. The filament may be attached to a ferrule and the ferrule may be press-fit into a lumen of a wedge.

In various embodiments, a filament may have a preformed shape forming an end of the filament into a shape when released from the outer sheath of the deployment catheter, e.g., a loop, an ovoid, an ellipse, a slot, a rectangle, a combination thereof, or the like. The filament end may be any shape for a user to engage an instrument with the tether. A filament may comprise any material, e.g., nitinol, a polymer, a rubber, nylon, stainless steel, nickel titanium, combinations thereof, or the like.

In various embodiments, a grasper may comprise stamped and bent sheet metal or plastic. The grasper may comprise a single piece or multiple pieces, e.g., two symmetrical pieces extending along a longitudinal axis of a clip. The jaws of a grasper may have protrusions at a distal end of the grasper configured to engage tissue. The jaws of a grasper may touch each other in the closed configuration or there may be a space between the jaws in the closed configuration. The ends of the jaws may spread apart from each other about 1 millimeter to about 5 millimeters, e.g., about 2 millimeters to about 3 millimeters, in the open configuration, although the open configuration may be any width desired based on the grasper and the wedge configuration.

With reference to FIGS. 10A-10F, a method of clipping a target tissue 1070 within a patient according to an embodiment of the disclosure is illustrated including a delivery catheter that includes an outer sheath 1066 (which may optionally be an introducer catheter) containing a tissue retraction/traction system. It will be appreciated that any of the above-described clip configurations or embodiments, or alternate clips, may be used in the following method. The outer sheath 1066 is insertable within a body lumen 1075 of the patient and positionable toward a target location of the target tissue 1070 for retraction and dissection. The outer sheath 1066 of the deployment catheter contains an instrument sheath 1062. The instrument sheath 1062 contains a medical instrument 1060 that is engaging a filament 1010 of a first tissue clip 1001. The first clip 1001 is attached to an elongate tether member 1050 via an attachment member 1016. A second clip 1002 is also attached to the elongate tether member 1050 via an attachment member 1016 at an end of the tether member 1050 opposite the end to which the first clip 1001 is attached. This system may be pre-loaded into the outer sheath 1066 as described with reference to FIG. 2D.

Figure 10A:
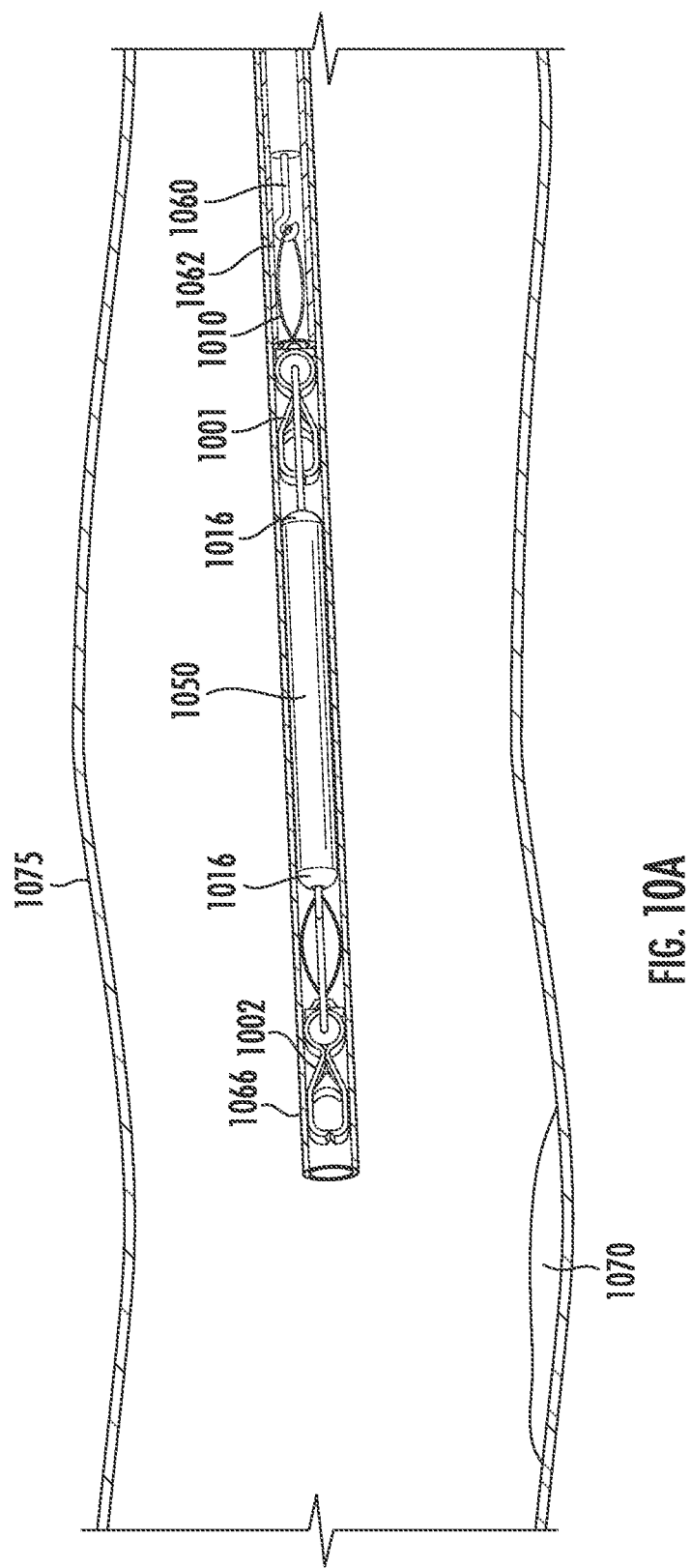
FIGS. 10A-10F illustrate a tissue clip system and retraction/traction procedure within a body lumen of a patient, in accordance with an embodiment of the present disclosure.
Figure 10B:
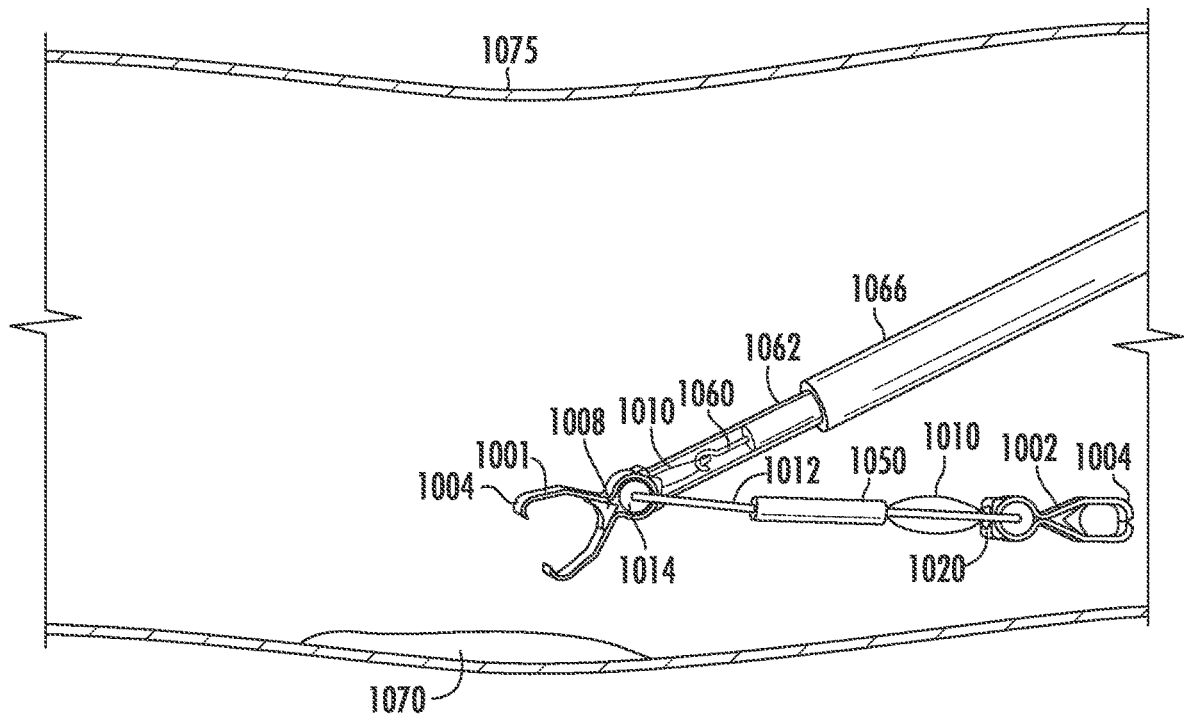

With reference to FIG. 10B, the instrument sheath 1062 is advanced distally through the outer sheath 1066 such that the second clip 1002, elongate tether member 1050, and first clip 1001 are pushed distally out of the outer sheath 1066 generally toward the target location of the target tissue 1070.

Figure 10C:
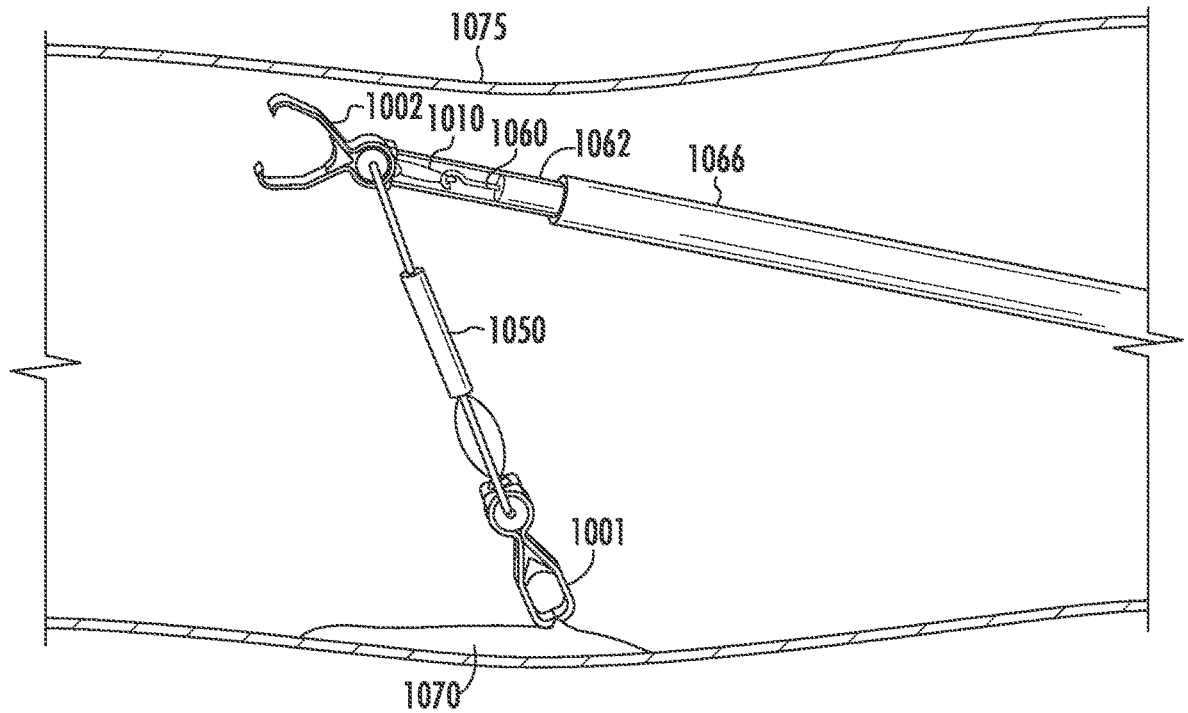

The first clip 1001 is held near the distal end of the instrument sheath 1062 by the instrument 1060 engaging the filament 1010 of the first clip 1001. The retainer 1014 and jaws 1004 of the first clip 1001 are swung about the hinge 1012 such that the hinge is moved away from the area between the jaws 1004 of the first clip 1001 and the target tissue 1070. The elongate tether member 1050 and second clip 1002 may also rotate away from the target location of the target tissue 1070. The second clip 1004 is in the closed configuration because the filament 1010 of the second clip 1002 is not engaged by the medical instrument 1060. The filament 1010 of the first clip 1001 is in tension from the medical instrument 1060 engaging the filament 1010 and pulling the first clip 1001 in a proximal direction toward the end of the instrument sheath 1062. Additional force in a proximal direction by the instrument 1060 on the filament 1010 may move the wedge 1008 toward the retainer 1014, opening the jaws 1004 such that the first clip 1001 is in the open configuration and is ready to engage the target tissue 1070. The first clip 1001 in the open configuration may be moved toward the target location of the target tissue 1070 via the instrument sheath with or without the outer sheath 1066, and the tension in the filament 1010 of the first clip 1001 may be released to transition the first clip 1001 into the closed configuration and fix it to the target tissue 1070 by engaging the jaws 1004 of the first clip 1001 with the target tissue 1070, as illustrated in FIG. 10C. The instrument 1060 may then release the filament 1010 of the first clip 1001 by extending distally out of the instrument sheath 1062, and the instrument sheath 1062 may be moved such that the first clip 1001 is completely deployed from the instrument sheath 1062. The instrument sheath 1062 is then moved toward the filament 1010 of the second clip 1002. The instrument 1060 engages the filament 1010 of the second clip 1002 and retracts in a proximal direction, pulling the filament 1010 into the instrument sheath 1062. Because the filament 1010 of the second clip 1002 has a shape memory loop that extends outwardly, the medical instrument 160 may more easily engage the filament 1010. The filament 1010 of the second clip 1002 is pulled further into the instrument sheath 1062 until the alignment member 1020 is substantially axial with the lumen of the instrument sheath 1062. The filament 1010 of the second clip 1002 is then pulled into tension by the instrument 1060 to transition the second clip 1002 from the closed configuration of FIG. 10B into the open configuration of FIG. 10C as the second clip 1002 is moved toward a portion of the wall of the body lumen 1075. The jaws of the second clip 1002 are placed into engagement with the wall of the body lumen 1075 and the filament 1010 is released from tension such that the second clip 1002 transitions into the closed configuration, engaging the wall of the body lumen 1075.

Figure 10D:
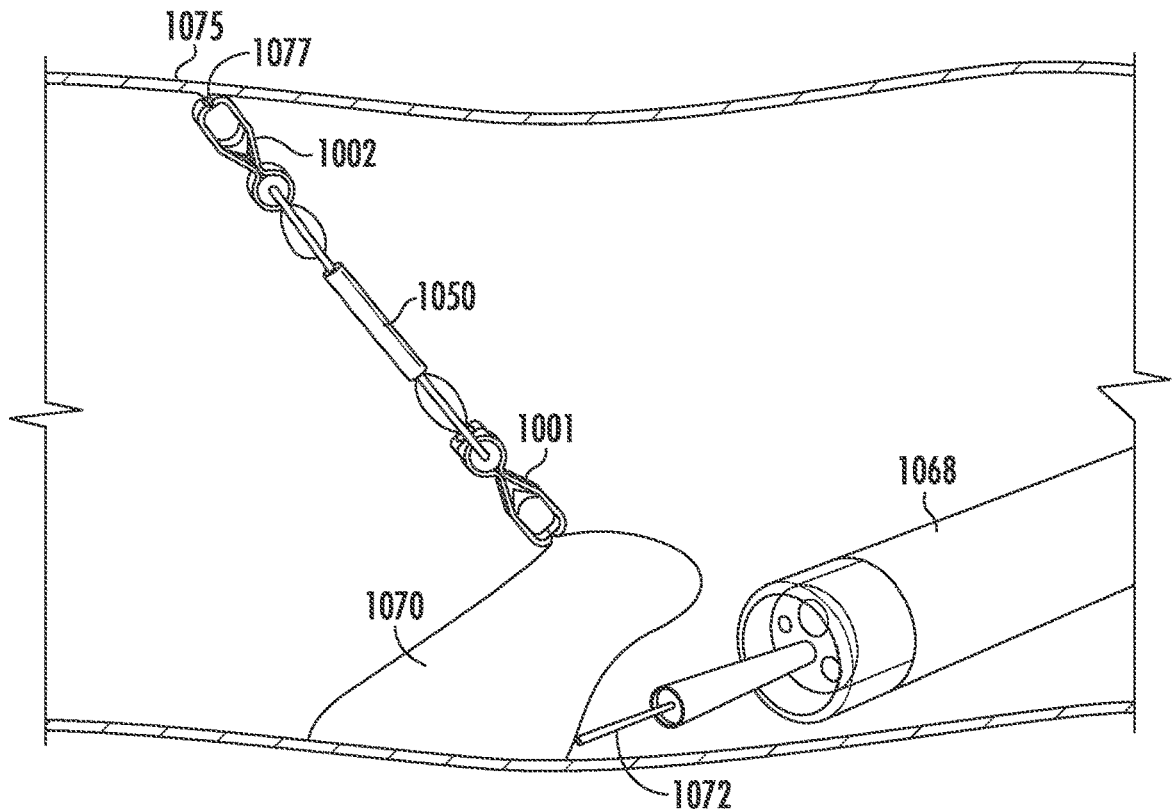

As illustrated in FIG. 10D, with the first clip 1001 engaging the target tissue 1070 and the second clip 1002 engaging a second location 1077 of tissue of the wall of the body lumen 1075, the elongate tether member 1050 is under tension that retracts the target tissue 1070 toward the second clip 1002 as a resecting tool 1072 resects the target tissue 1070 from a working channel of a scope 1068, which may or may not be the same outer sheath 1066. Once the tension in the elongate tether member 1050 is no longer desirable for further resecting the target tissue 1070 (e.g., the portion of the target tissue 1070 that needs to be resected is no longer visible because the target tissue 1070 is no longer being substantially lifted), the instrument 1060 and instrument sheath 1062 are reintroduced toward the second clip 1002.

Figure 10E:
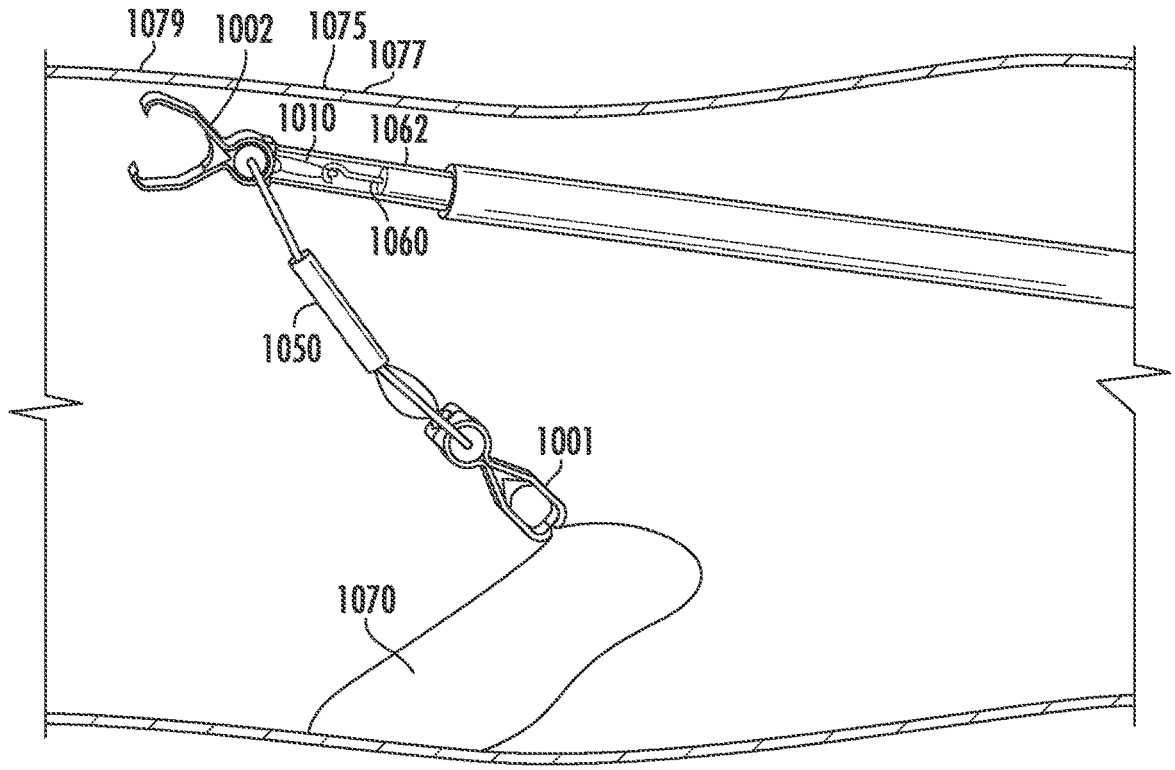

As illustrated in FIG. 10E, the instrument 1060 re-engages the filament 1010 of the second clip 1002 as it did in FIG. 10C to reposition the second clip 1002 to obtain tension in the elongate tether member 1050. The second clip 1002 is transitioned to the open configuration by the instrument 1060 and instrument sheath 1062, and the second clip 1002 is repositioned toward a third target location 1079 of tissue of the wall of the body lumen 1075 that is farther from the first clip 1001 than the second target location 1077 of tissue of the wall of the body lumen 1075.

Figure 10F:
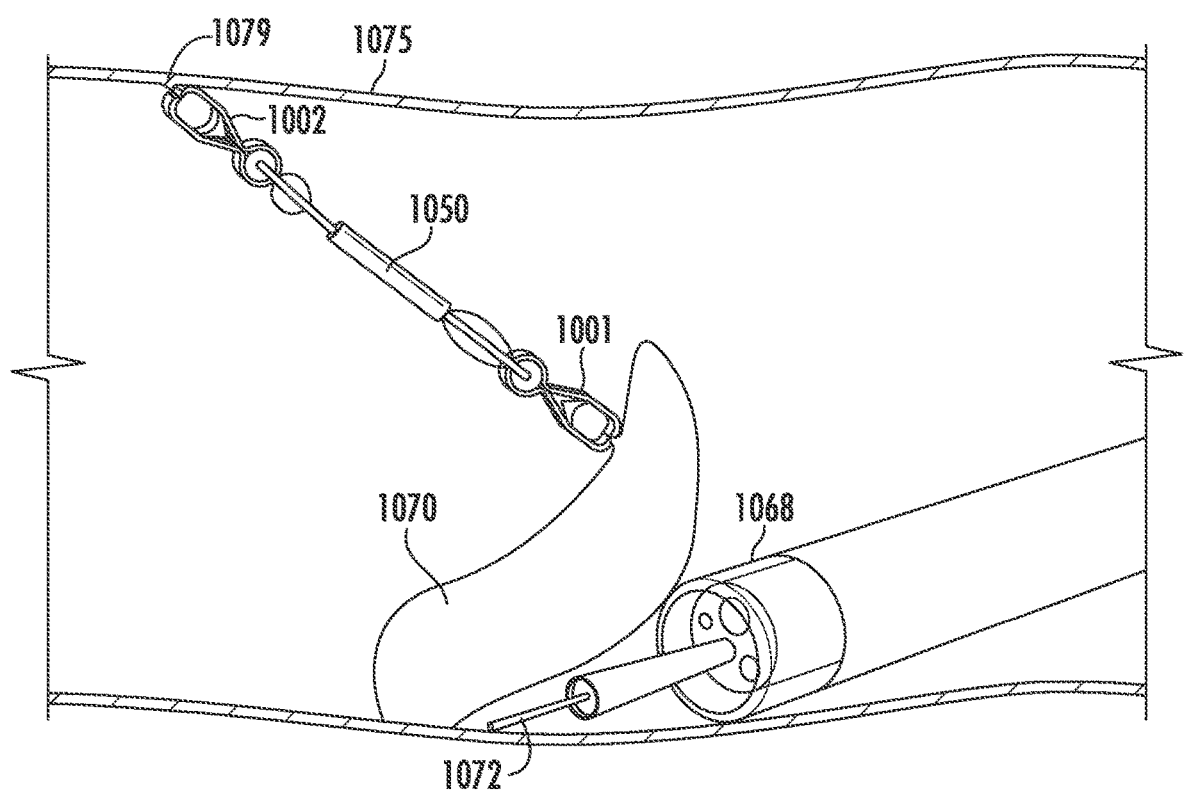

As illustrated in FIG. 10F, with tension restored in the elongate tether member 1050, the resecting tool 1072 may be reintroduced to continue resecting the target tissue 1070 such that the target tissue 1070 is dissected from the body lumen 1075. The second clip 1002 may then be retrieved using the instrument 1060, instrument sheath 1062, and outer sheath 1066 with the dissected target tissue 1070 attached to the first clip 1001 to be removed from the patient. In some embodiments, the tether 1050 and clips 1001, 1002 may additionally or alternatively be used to grasp a portion of a tissue or a portion of an organ and position it out of the way, e.g., of a working area for a medical professional, to access a target tissue area. For example, both clips 1001, 1002 may be attached to the body lumen wall 1075 with a portion of a tissue held against the body lumen wall 1075 wall by tether 1050.

Devices according to the embodiments described, and in accordance with other embodiments of the present disclosure, alone or in a system or kit or as part of a method or procedure, including with other accessories, may be used in cavities, lumens, tracts, vessels, and organs of the body, such as to access, treat, or diagnose conditions in the peritoneal, abdominal, bronchial, or thoracic cavities; vascular vessels; gastrointestinal or urinary tract; uterus, bladder, lung, or liver organs, etc.

Variations, modifications, and other implementations of the present disclosure in addition to the various embodiments described herein will occur to those of ordinary skill in the art. Accordingly, the present disclosure is to be defined not by the preceding illustrative description but instead by the following claims:

What is claimed is:

1. A tissue clip, comprising:
   a grasper having a first end and a second end, the grasper including a spring portion at the second end, and jaws at the first end biased toward each other by the spring portion into a closed configuration to grasp tissue;
   an actuator mounted with respect to the grasper; and
   a loop coupled to the actuator;
   wherein the actuator is movable upon movement of a separately formed instrument releasably coupled to the loop to move the actuator relative to the spring portion and the jaws to cause the spring portion to move the jaws from the closed configuration to an open configuration.

2. The clip of claim 1, further comprising a filament extending away from the clip to a distal end of the filament forming the loop.

3. The clip of claim 2, further comprising an alignment member at the second end of the grasper, wherein the filament extends through a channel of the alignment member, and wherein the alignment member is configured to align the grasper with a lumen of an instrument sheath.

4. The clip of claim 1, wherein the actuator is a wedge slidably disposed between the jaws and movable toward the spring portion to cause the jaws to move to the open configuration.

5. A tissue, further comprising:
   a grasper having a first end and a second end, the grasper including jaws at the first end biased toward each other into a closed configuration to grasp tissue;
   an actuator mounted with respect to the grasper;
   a loop coupled to the actuator; and
   a filament extending away from the clip to a distal end of the filament forming the loop;
   wherein the actuator is movable upon movement of a separately formed instrument releasably coupled to the loop to move the actuator relative to the jaws to cause the jaws to move from the closed configuration to an open configuration.

6. The clip of claim 5, further comprising an alignment member at the second end of the grasper, wherein the filament extends through a channel of the alignment member, and wherein the alignment member is configured to align the grasper with a lumen of an instrument sheath.

7. The clip of claim 1, wherein the spring portion is movable into the actuator.

8. The clip of claim 7, wherein the actuator comprises a capsule into which the spring portion is movable to cause the jaws to move to the open configuration.

9. The clip of claim 1, wherein the actuator is positioned between the jaws of the grasper.

10. The clip of claim 1, wherein the grasper is movable into the actuator to cause the jaws to move to the open configuration.

11. The clip of claim 1, further comprising a hinge coupled to the second end of the grasper.

12. The clip of claim 11, wherein a first end of the hinge is disposed within a retainer disposed within the second end of the grasper, and a second end of the hinge includes an attachment member configured to attach to a tether.

13. A tissue clip system comprising:
    an elongate tether member having a first end and a second end;
    a first tissue clip coupled to the first end of the elongate tether member, the first tissue clip comprising a first grasper having a first end and a second end, first jaws at the first end of the first grasper which are biased toward each other, and a first actuator mounted with respect to the first jaws, wherein relative movement of the first actuator with respect to the first jaws causes the first jaws to move from a closed configuration to an open configuration;
    a second tissue clip coupled to the second end of the elongate tether member, the second tissue clip comprising a second grasper having a first end and a second end, second jaws at the first end of the second grasper which are biased toward each other, and a second actuator mounted with respect to the second jaws, wherein relative movement of the second actuator with respect to the second jaws causes the second jaws to move from a closed configuration to an open configuration; and
    a deployment catheter having an engagement end slidably disposed within a lumen of an instrument sheath and configured to engage at least one of the actuators.

14. The system of claim 13, where the first grasper of the first tissue clip comprises a first spring portion at the second end of the first grasper biasing the first jaws toward each other.

15. The system of claim 14, wherein the first actuator of the first tissue clip is movable relative to the first spring portion of the first tissue clip to cause the first spring portion to more the first jaws apart.

16. The system of claim 13, wherein the first actuator of the first tissue clip is positioned between the first jaws of the first grasper of the first tissue clip.

17. The system of claim 13, wherein the first grasper of the first tissue clip is movable into the first actuator to cause the first jaws to move to the open configuration.

18. The system of claim 13, further comprising a first hinge having a first end coupled to the second end of the first grasper of the first tissue clip, and a second end coupled with the elongate tether member.

\* \* \* \* \*